United States Patent [19]

Polaschegg

[11] Patent Number: 5,522,998
[45] Date of Patent: Jun. 4, 1996

[54] HEMODIALYSIS APPARATUS HAVING A SINGLE BALANCE CHAMBER AND METHOD OF DIALYZING BLOOD THEREWITH

[75] Inventor: Hans-Dietrich Polaschegg, Oberursel, Germany

[73] Assignee: Fresenius AG, Bad Homburg, Germany

[21] Appl. No.: 210,674

[22] Filed: Mar. 18, 1994

[30] Foreign Application Priority Data

Mar. 18, 1993 [DE] Germany .......................... 43 08 586.5

[51] Int. Cl.[6] .......................... B01D 61/24; B01D 61/28; B01D 61/32
[52] U.S. Cl. .................. 210/646; 210/85; 210/87; 210/88; 210/89; 210/96.2; 210/97; 210/98; 210/109; 210/117; 210/134; 210/138; 210/252; 210/257.2; 210/258; 210/321.71; 210/321.72; 210/645; 210/739; 210/929
[58] Field of Search ..................................... 210/645, 646, 210/929, 739, 85, 87, 88, 89, 96.2, 97, 98, 101, 103, 109, 117, 134, 136, 138, 139, 252, 257.2, 258, 321.72, 321.71

[56] References Cited

U.S. PATENT DOCUMENTS

| | | | |
|---|---|---|---|
| 4,267,040 | 5/1981 | Schäl | 210/929 |
| 4,530,759 | 7/1985 | Schäl | 210/929 |
| 4,618,343 | 10/1986 | Polaschegg | 210/646 |
| 4,770,769 | 9/1988 | Schael | 210/96.2 |
| 4,857,199 | 8/1989 | Cortial | 210/646 |
| 4,971,700 | 11/1990 | Tsuji et al. | 210/646 |
| 4,997,570 | 3/1991 | Polaschegg | 210/646 |
| 5,009,775 | 4/1991 | Tsuji et al. | 210/929 |

FOREIGN PATENT DOCUMENTS 2544258  4/1977  Germany .

*Primary Examiner*—John Kim
*Attorney, Agent, or Firm*—W. G. Fasse; W. F. Fasse

[57] ABSTRACT

In a dialysis apparatus having a dialyzer and a single balance chamber, the internal volume of the balance chamber is preferably at most ⅔ of the volume of the dialysis fluid chamber within the dialyzer. As a result, during the dialysis fluid recirculation cycle, at most ⅔ of the volume of fluid within the dialysis fluid chamber will be replaced by fresh dialysis fluid. Preferably, the duration of the recirculation cycle is approximately equal to the duration of the balance chamber filling cycle.

22 Claims, 1 Drawing Sheet

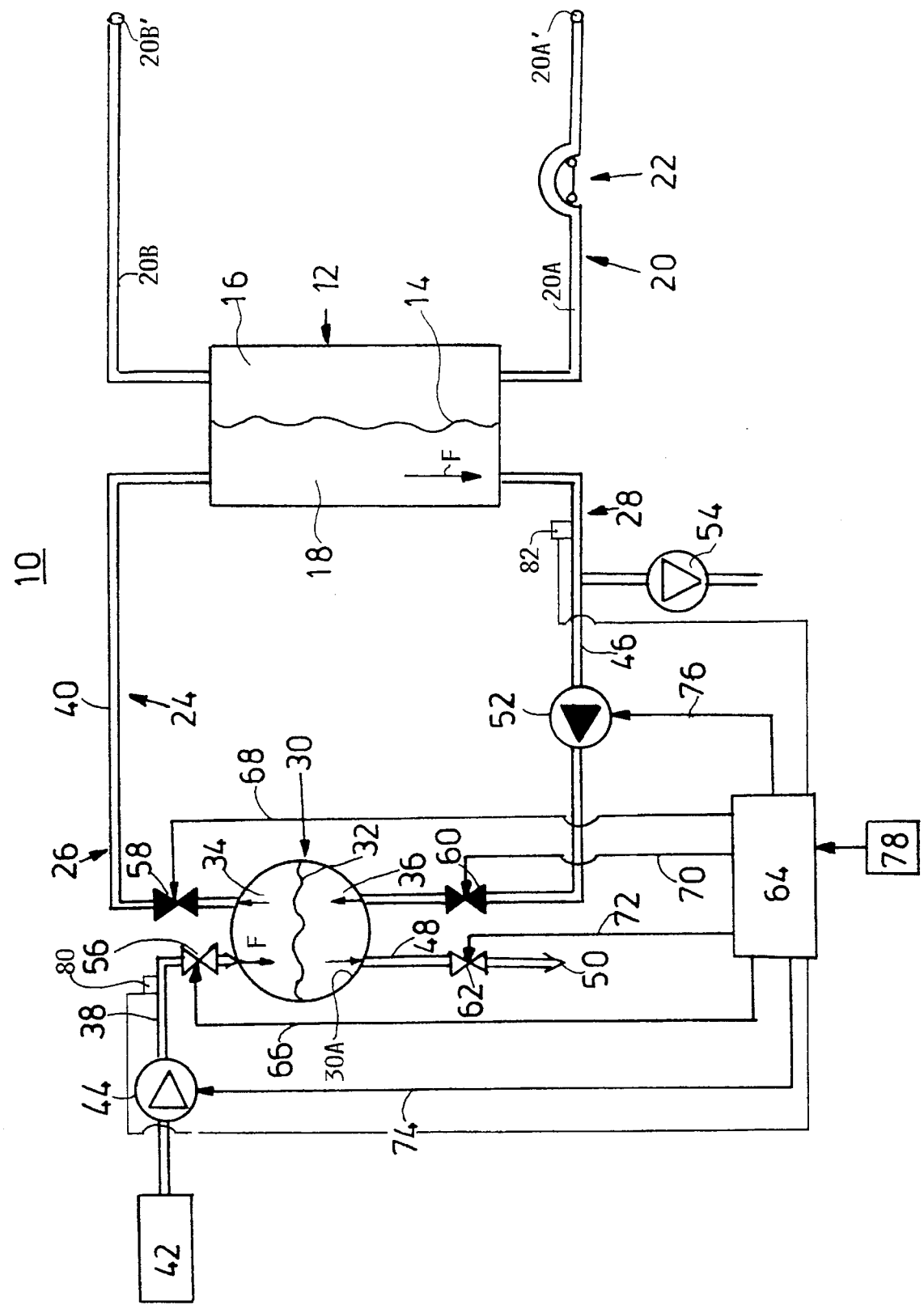

HEMODIALYSIS APPARATUS HAVING A SINGLE BALANCE CHAMBER AND METHOD OF DIALYZING BLOOD THEREWITH

FIELD OF THE INVENTION

The invention relates to a hemodialysis apparatus having a dialyzer, which is divided by a semipermeable membrane into a dialysis fluid chamber and a blood chamber, as well as a dialysis fluid source and a single balance chamber, which is divided by a displaceable partition wall into two partial balance chambers, and necessary conduits to interconnect the dialysis fluid source to one of the partial balance chambers, which is further connected to the blood chamber of the dialyzer, which in turn is connected to the other partial balance chamber.

BACKGROUND INFORMATION

Hemodialysis apparatus of the above described type generally have inlet and outlet conduits into the blood chamber of the dialyzer to form a blood flow path through the blood chamber. On the other hand, a dialysis fluid flow path is formed, starting at the dialysis fluid source and ending at a dialysis fluid outlet or drain. Separate dialysis fluid conduits connect, in series, the dialysis fluid source, the fresh dialysis fluid side or first partial chamber of the balance chamber, the dialysis fluid chamber of the dialyzer, the used dialysis fluid side or second partial chamber of the balance chamber, and finally the used dialysis fluid outlet. Furthermore, an ultrafiltration unit is connected to the fluid flow conduit between the dialysis fluid chamber of the dialyzer and the used dialysis fluid side or second partial chamber of the balance chamber.

A first group of valves or other shut-off devices includes a first valve arranged between the dialysis fluid source and the fresh fluid side of the balance chamber and a fourth valve arranged between the used fluid side of the balance chamber and the used fluid outlet. A second group of valves or shut-off devices includes a second valve arranged between the fresh fluid side of the balance chamber and the dialysis fluid chamber of the dialyzer and a third valve arranged between the dialysis fluid chamber and the used fluid side of the balance chamber. A dialysis fluid supply pump is arranged in the conduit between the dialysis fluid source and the fresh fluid side of the balance chamber. A second dialysis fluid pump is arranged in the conduit between the dialysis fluid chamber of the dialyzer and the used fluid side of the balance chamber.

A control and regulation unit controls the pumps and valves so that in a first operating cycle the dialysis fluid supply pump is activated and the first group of valves, including the first and fourth valves, is activated or opened, while the second group of valves, including the second and third valves, is deactivated or closed. In a second operating cycle, the second dialysis fluid pump is activated and the second group of valves, including the second and third valves, is activated or opened, while the valves of the first group are correspondingly deactivated or closed.

Hemodialysis apparatus using volumetric ultrafiltration control, typically operate with a closed dialysis fluid system, from which predetermined amounts of the dialysis fluid are removed or withdrawn. Because the system is closed, the withdrawn volume of fluid is made up or replaced by a corresponding volume of fluid which diffuses through the dialyzer membrane from the extracorporeal blood flow circuit and thus from the patient.

In order to achieve a substantially steady and constant flow of dialysis fluid from the dialysis fluid source on the one hand, to the dialyzer on the other hand, despite the closed arrangement of the fluid system, numerous hemodialysis apparatus include a balancing device that comprises two balance chambers. Each of the two balance chambers is divided into two partial chambers by a displaceable membrane. Thus, a total of four balance chamber portions or partial chambers is provided. Each of these four partial chambers is connected to an inflow conduit and an outflow conduit, resulting in a total of eight conduit connections to the four partial chambers of the two balance chambers. A respective shut-off device, such as a valve, is arranged in each one of the conduits, resulting in a total of eight separate shut-off valves.

The balance chambers are interconnected by conduits in such a manner, and the shut-off valves are appropriately controlled, so that one of the balance chambers is in a respective filling and emptying operating cycle while the other balance chamber is in the dialysis operating cycle. That is to say, in one balance chamber a first partial chamber is being filled with fresh dialysis fluid, whereby the displaceable membrane is displaced to make this first partial chamber larger, while tending to make the second partial chamber smaller, so that the used dialysis fluid is emptied from the second partial chamber. While the one balance chamber is in this filling and emptying operating cycle, the other balance chamber is in the dialysis operating cycle, whereby fresh fluid is pumped from the fresh fluid side of the balance chamber through the dialyzer and returned to the used fluid side of the balance chamber. As soon as the fresh dialysis fluid of the second balance chamber has been completely delivered through the dialysis fluid chamber of the dialyzer, then a cyclically alternating, controlled switching of the two balance chambers is carried out. As a result, the balance chamber of which the fresh fluid side has been filled now operates in a dialysis cycle, while the other balance chamber of which the fresh fluid side has been emptied is again refilled. In this manner, at each moment, one of the balance chambers is being filled with fresh dialysis fluid while the fresh fluid that has just been filled into the other balance chamber is being circulated through the dialyzer. With such an arrangement, it is possible to achieve a nearly continuous and uniform flow of dialysis fluid through the dialyzer. The flow is only momentarily interrupted during the switching over from one of the balance chambers to the other balance chamber. Such systems having two balance chambers, are, for example, described in the German Patent Publication 2,838,414, corresponding to U.S. Pat. No. 4,770,769 (Schael), issued Sep. 13, 1988.

In contrast to the continuously operating dialysis systems or balancing systems having two balance chambers, systems having a single, large balance chamber or fluid reservoir chamber also exist. Such a system is described, for example, in the German Patent Publication 2,544,258 or can be represented by the dialysis apparatus marketed under the Tradename and Model Monitral by the company Hospal AG located at Basel, Switzerland. In dialysis apparatus having such a large single balance chamber, the balance chamber is typically filled as quickly as possible in a first operating cycle. Then, in a second operating cycle, which is carried out over a substantially longer period of time, the dialysis fluid is circulated from the filled balance chamber through the dialysis fluid chamber of the dialyzer. In that manner, it is achieved that the time interval during which dialysis fluid does not flow through the dialyzer is kept relatively short.

Both of the above described systems are very costly and complicated, both in terms of the technology of the apparatus and instrumentation, as well as the technology of the control arrangements. On the one hand, the method and apparatus using a double balance chamber requires an extra balance chamber and an extra set of associated valves and conduits as compared to the single balance chamber method and apparatus. On the other hand, the method and apparatus using a single balance chamber makes high demands on the filling performance, which can lead to an unusually early wear and possible failure of the fluid pumps.

OBJECTS OF THE INVENTION

In view of the above it is the aim of the invention to achieve the following objects singly or in combination:
- to provide a hemodialysis apparatus of the above described type which is much simpler in terms of the required apparatus components, but which achieves at least the same dialysis effectiveness as the above described dialysis apparatus of the prior art;
- to provide a hemodialysis apparatus of the above described type with a single balance chamber having a relatively small volume;
- to provide such a hemodialysis apparatus which achieves a good dialysis effect even if the dialysis fluid is only circulated through the dialysis fluid chamber of the dialyzer in an intermittent or discontinuous manner;
- to provide such a single balance chamber dialysis apparatus, wherein the balance chamber has a volume at most two thirds of the volume of the dialysis fluid chamber of the dialyzer;
- to provide a method and apparatus to control a dialysis fluid pump in such a dialysis apparatus to deliver fresh dialysis fluid of at most two thirds of the volume of the dialysis fluid chamber of the dialyzer during each recirculation cycle; and
- to provide a method and apparatus for a single balance chamber dialysis apparatus in which the dialysis fluid is circulated through the dialyzer for approximately the same length of time in a dialyzing cycle as the duration of the refilling cycle of the balance chamber.

SUMMARY OF THE INVENTION

The above objects have been achieved in a single balance chamber dialysis apparatus and method according to the invention, in which at most two thirds of the volume of fluid in the dialysis fluid chamber of the dialyzer is replaced with fresh dialysis fluid by the dialysis fluid pump operating during a recirculation cycle. It was determined unexpectedly according to the invention that it is irrelevant to the exchange efficiency of the dialyzer whether the dialysis fluid flow through the dialyzer is uniform and continuous as in the double balance chamber method or whether the fluid flow is discontinuous as results in the single balance chamber method, as long as the volume of the balance chamber is at most two thirds of the volume of the dialysis fluid chamber of the dialyzer.

This statement of the unexpected discovery assumes that all of the fresh dialysis fluid that has been filled into the entire balance chamber volume is pumped through the dialysis fluid chamber of the dialyzer by the return line circulation pump during a circulation cycle, as is typically the case. However, it should be understood that it is not necessary to pump the entire volume of fresh dialysis fluid contained in the balance chamber through the dialyzer in each circulation cycle. Therefore, the invention also covers the embodiment in which the return line circulation pump simply pumps a controlled volume of dialysis fluid out of the balance chamber corresponding to at most two thirds of the volume of the dialysis fluid chamber of the dialyzer during each circulation cycle. Thus, in such an embodiment the actual volume of the balance chamber is independent of, e.g. can be larger than, the volume of the dialysis fluid chamber, but rather depends only on a proper volume or time based control of the dialysis fluid pump, with consideration of its pumping rate. This is especially important, for example, if the dialysis apparatus is to be used with various dialyzers having different dialysis fluid chamber volumes.

Thus, the general determinative point of the invention is that the fluid volume delivered during one fluid delivery period is smaller than the fill volume of the dialysis fluid chamber of the dialyzer. According to a preferred embodiment of the invention it is further advantageous if the mean flow rate of the dialysis fluid is approximately constant or uniform, that is to say that approximately equal time durations apply, for the filling cycle as for the circulation cycle.

It should be noted that the flow or current of the dialysis fluid through the dialyzer and the diffusion of urine component substances through the membrane of the dialyzer are independent from each other. The flow direction or current of the dialysis fluid follows the decreasing pressure gradient caused by the dialysis fluid pump, i.e. the return line circulation pump, and runs in a direction essentially parallel to the surface of the membrane. On the other hand, the diffusion is directed along the concentration gradient between the blood and the dialysis fluid, i.e. substantially perpendicularly to the surface of the membrane.

As a result, the above described two directional components are superimposed in the motion of a urine component molecule. In order that a molecule ultimately leaves the immediate area of the membrane and exits from the outlet of the dialyzer, it is therefore simply necessary that it reaches a certain distance from the membrane and subsequently is transported to the outlet. In this context it is irrelevant what distance away from the surface of the membrane the molecule has achieved. Furthermore, the current flow behavior in the dialysis fluid region is irrelevant in any event, as long as the molecule diffuses through the membrane or is still located in the blood region.

According to the invention, it is thereby advantageous that by maintaining the claimed volume ratios, the fluid portions flowing within the dialysis fluid chamber are not flushed or sluiced out of the chamber by the circulation of the dialysis fluid through the chamber. Furthermore, the loss of effectiveness only becomes significant once the volume of the fluid exchange exceeds the claimed volume ratio.

Because the dialysis-side fill volume, that is to say the volume of the dialysis fluid chamber, of typical capillary dialyzers is approximately 150 ml, for example, in the F40 dialyzer of the company Fresenius AG of Bad Homburg, Federal Republic of Germany, the circulation volume for using such a dialyzer should at most be approximately 100 ml and preferably be below 75 ml and most preferably be about 30 ml.

BRIEF DESCRIPTION OF THE FIGURE

In order that the invention may be clearly understood, it will now be described, by way of example, with reference to the single FIGURE, which schematically shows a dialysis apparatus having a single balance chamber according to the invention.

DETAILED DESCRIPTION OF PREFERRED EXAMPLE EMBODIMENTS AND OF THE BEST MODE OF THE INVENTION

The FIGURE shows a dialysis apparatus 10 generally including a dialyzer 12, a balance chamber 30, a dialysis fluid source 42, as well as pumps, valves and conduits to be described in the following. The dialyzer 12 is divided by a semipermeable membrane 14 into a blood chamber 16 and a dialysis fluid chamber 18. Blood flow conduits 20A and 20B are connected to the blood flow chamber 16 to establish a blood flow path 20 therethrough. A blood pump 22 is arranged in the blood conduit 20A to pump blood through the blood chamber 16. The ends 20A' and 20B' of the blood conduits 20A and 20B are to be connected to the circulatory system of a patient, for example. The blood flow path 20 is merely shown schematically and is of a conventional construction.

A dialysis fluid supply conduit 26 and a dialysis fluid removal conduit 28 are connected to the dialysis fluid chamber 18 to establish a dialysis fluid path or circuit 24. Furthermore, the single balance chamber 30 is divided by a displaceable partition wall 32, such as a flexible membrane, into a first partial chamber 34 of the balance chamber for receiving fresh dialysis fluid and a second partial chamber 36 of the balance chamber for receiving used dialysis fluid.

The dialysis fluid supply conduit 26 is connected to the partial chamber 34 of the balance chamber, in that the supply conduit 26 is divided into a first supply conduit component 38 and a second supply conduit component 40, which are both connected to the partial chamber 34. One end of the first supply conduit component 38 is connected to the dialysis fluid source 42 and the other end opens into the first partial chamber 34, as mentioned above. A dialysis fluid supply pump 44 is arranged in the first supply conduit component 38. The second supply conduit component 40 is connected at one end to the first partial chamber 34 and opens at its other end into the dialysis fluid chamber 18 of the dialyzer 12. Fluid flow is shown by arrows F.

The dialysis fluid removal conduit 28 extends through the second partial chamber 36 of the balance chamber in that it is divided into a first fluid removal conduit component 46 and a second fluid removal conduit component 48, which are each connected to the second partial chamber 36. In this context, the first removal conduit component 46 begins at the dialysis chamber 18 and opens at its other end into the second partial chamber 36 of the balance chamber, while the second removal conduit component 48 begins at the second partial chamber 36 and opens into a used fluid outlet or drain 50. Furthermore, a dialysis fluid pump 52 is arranged in the first fluid removal conduit component 46. Additionally, in a typical manner an ultra-filtration unit 54 is provided branching off of the first fluid removal conduit component 46. More generally as is known in the art, the pump 52 and the ultra-filtration unit 54 can be arranged anywhere in the circuit downstream of the second valve 58 (described below) and upstream of the third valve 60 (described below).

The above mentioned valves are arranged as follows. Respectively adjacent to the first and second partial chambers 34 and 36 of the balance chamber 30, a first valve 56 is arranged in the first supply conduit component 38, a second valve 58 is arranged in the second supply conduit component 40, a third valve 60 is arranged in the first fluid removal conduit component 46 and a fourth valve 62 is arranged in the second fluid removal conduit component 48. The first valve 56 and the fourth valve 62 together can be considered to form a first group or pair of valves. The second valve 58 and the third valve 60 together can be considered to form a second pair or group of valves. All the valves 56, 58, 60 and 62 are connected to a control and regulation unit 64 via control lines 66, 68, 70 and 72 respectively. Furthermore, the pumps 44 and 52 are connected to the control and regulation unit 64 via control lines 74 and 76 respectively.

As shown in the FIGURE, the first group or pair of valves 56 and 62 as well as the pump 44 are shown with light or non-filled symbols. On the other hand, the second group or pair of valves 58 and 60 as well as the pump 52 are shown with dark or filled-in symbols. The different graphic representation indicates the different respective activated state of the components in response to control signals provided by the control and regulation unit 64 as will be described below.

The dialysis apparatus 10 according to a first embodiment of the invention is particularly characterized in that the volume of the dialysis fluid chamber 18 on the one hand, and the volume of the balance chamber 30, which is made up of the volumes of the first partial chamber 34 and the second partial chamber 36, on the other hand, are related to each other by a ratio of at most 1:2/3. According to a second embodiment of the invention, the dialysis fluid pump 52 delivers an amount of dialysis fluid during one circulating cycle corresponding to at most ⅔ of the volume of the dialysis fluid chamber 18.

Preferred volume ratios are at most 50% and especially at most 30% and most preferably at about 20% of the volume of the dialysis fluid chamber 18. Of the two embodiments, however, the first embodiment is preferred, that is to say the embodiment in which the total volume of the balance chamber 34 is limited and defined relative to the volume of the dialysis fluid chamber 18.

The dialysis apparatus 10 operates according to the method of the invention as described in the following. In one working cycle the first pair of valves 56 and 62 and the dialysis fluid supply pump 44 are activated, that is to say the valves 56 and 62 are opened to allow fluid flow therethrough and the pump 44 is turned on to pump dialysis fluid. At the same time, the second pair of valves 58 and 60 remain closed and the pump 52 is deactivated. On the other hand, the pump 52 can be allowed to remain activated, that is to say to continue pumping in an idling mode against the closed valve 60.

In this operating cycle, the dialysis fluid supply pump 44 delivers fresh dialysis fluid from the dialysis fluid source 42 into the first partial chamber 34 of the balance chamber 30, whereby the displaceable partition wall 32 is displaced so as to expand the volume of the first partial chamber 34 while reducing the volume of the second partial chamber 36 until the displaceable partition wall 32 is pressed against the inner wall 30A of the chamber 30. Through this operation, any used dialysis fluid present in the second partial chamber 36 will be pressed out of the balance chamber 30 through the open fourth valve 62 and into the outlet or drain 50.

As soon as the first partial chamber 34 has been filled with fresh dialysis fluid, the control unit 64 produces a switch-over signal that causes the first pair of valves 56 and 62 to close and the second pair of valves 58 and 60 to open, while also activating the dialysis fluid pump 52. Furthermore, the fluid supply pump 44 is either deactivated or allowed to continue running in an idling manner.

The switching-over of the valves and pumps establishes a second operating cycle in which the fresh dialysis fluid is delivered out of the first partial chamber 34 of the balance chamber into the dialysis fluid chamber 18 of the dialyzer 12. In the dialysis fluid chamber 18, the newly supplied fresh dialysis fluid partially displaces used dialysis fluid, which is caused to exit the dialysis fluid chamber 18 through the first fluid removal conduit component 46 and flow into the second partial chamber 36 of the balance chamber 30. There, the incoming used fluid displaces or moves the displaceable partition wall 32 while constantly reducing the volume of the first partial chamber 34 of the balance chamber 30 while simultaneously and correspondingly increasing the volume of the second partial chamber 36. As soon as the fluid delivery process is completed, that is to say when the first partial chamber 34 has been emptied, or when a predetermined quantity of dialysis fluid has been delivered, then a new control signal is produced by the control unit 64, which results in switching-over the state of the valves and pumps to reestablish the first operating cycle as described above.

The control of the operation of the apparatus and the switching from one operating cycle to the other as described above, can be carried out by a timing control depending on the delivery rate of the two pumps 44 and 52. In this manner, by selecting a proper time duration of each operating cycle, it can be ensured that at the end of each cycle, the balance chamber 30 is filled either with fresh dialysis fluid in the first partial chamber 34 or with used dialysis fluid in the second partial chamber 36.

It should also be noted as described above, that it is not necessary to pump out the entire volume of the chamber 30 in each operating cycle. Thus, if the dialysis fluid chamber 18 is too small, or the volume of the balance chamber 30 is too large to maintain the claimed proportional volume delivery of dialysis fluid while completely emptying the chamber 30, then it is a simple matter to appropriately time the duration of the two operating cycles to provide only the necessary proportional volume delivery without completely emptying the chamber 30 on each cycle.

On the other hand, it is also possible to trigger the switch-over signal as described above with the aid of a sensor 80, 82, such as a flow sensor or a pressure sensor, arranged respectively in the first supply conduit component 38 and the first fluid removal conduit component 46. These sensors are preferably flow sensors that detect the flow rate through the corresponding conduit. Upon detecting a decrease in the flow rate, the sensors produce a signal that is provided to the regulation and control unit 64. Finally, it is also possible to derive the switch-over signal by measuring or sensing the motor current of the pumps 44 and 52, because a sudden and sharp increase in the motor current will be detected when the pressure rises as the operating cycle comes to an end. Producing a switch-over signal in response to changes in the motor current of fluid pumps is described in the German Patent Publication 2,838,414, and the corresponding U.S. Pat. No. 4,770,769 (Schael), issued Sept. 13, 1988, especially at column 16 in the U.S. Patent, of which the disclosure is incorporated herein by reference.

According to a preferred embodiment of the invention, the fluid delivery rate of each of the two pumps 44 and 52 is approximately the same, so that approximately equal cycle durations will result for the filling cycle and the dialysis or circulation cycle.

According to the second embodiment of the invention, the quantity of dialysis fluid delivered to the dialysis fluid chamber 18 during a circulation cycle is solely dependent on the volume that is pumped by the dialysis fluid pump 52 and delivered to the dialysis fluid chamber 18. Further, according to the invention, an input device 78 may be connected to the control and regulation unit 64. By entering the appropriate data on the input device 78, the fluid delivery rate and delivery time of the pump 52 can be prescribed as desired so that a specific volume of dialysis fluid can be selected and determined in this manner. Furthermore, the volume of the specific dialysis fluid chamber 18 being used, which varies from dialyzer to dialyzer, can similarly be entered in the input device 78, so that the two volumes can be properly correlated to one another according to the invention. Finally, it is also possible to directly enter the volume ratio of the two volumes into the input device 78.

By operating the apparatus disclosed herein according to the method disclosed herein, it is possible to achieve nearly the same dialysis efficiency, while cutting the cost and complexity of the required apparatus components of the balancing device in half as compared to the various apparatus known in the art. According to the state of the art, only apparatus and methods that continuously deliver dialysis fluid will achieve successful results. Furthermore, according to the state of the art, the use of a single chamber would lead to a reduction in efficiency and an increase in the cost and complexity of apparatus components. Thus, the present invention has overcome the disadvantages of the various prior art attempts to solve the stated problems.

Although the invention has been described with reference to specific example embodiments, it will be appreciated that it is intended to cover all modifications and equivalents within the scope of the appended claims.

What I claim is:

1. A hemodialysis apparatus for providing a hemodialysis solution to the dialysis fluid chamber of a dialyzer, the dialysis fluid chamber having a dialysis chamber volume, said hemodialysis apparatus comprising a balance chamber divided by a displaceable partition wall into a fresh fluid partial chamber and a used fluid partial chamber, a first pump that delivers a controlled fill volume of fluid during a filling operating cycle, a first shut-off device, a dialysis fluid source connected through said first pump and said first shut-off device to said fresh fluid partial chamber, a second shut-off device connected downstream of said fresh fluid partial chamber and having an outlet so arranged that it can be connected to the dialysis fluid chamber of the dialyzer, a third shut-off device connected upstream of said used fluid partial chamber and having an inlet so arranged that it can be connected to the dialysis fluid chamber of the dialyzer, a second pump arranged downstream of said second shut-off device and upstream of said third shut-off device to deliver a controlled circulation volume of fluid to the dialysis fluid chamber of the dialyzer during a circulating operating cycle when the dialyzer is connected between said second and third shut-off devices, an ultrafiltration unit connected downstream of said second shut-off device and upstream of said third shut-off device, a fourth shut-off device connected to said used fluid partial chamber, a used fluid outlet provided downstream from said fourth shut-off device, and a control unit connected for control transmission to each of said shut-off devices, wherein said control unit closes said second and third shut-off devices to end said circulating operating cycle and opens said first and fourth shut-off devices to begin said filling operating cycle and closes said first and fourth shut-off devices to end said filling operating cycle and opens said second and third shut-off devices to begin said circulating operating cycle, and wherein said controlled circulation volume of fluid delivered by said second pump to the dialysis fluid chamber during said circulating operating cycle is at most ⅔ of the dialysis chamber volume.

2. The hemodialysis apparatus of claim 1, comprising only one said balance chamber and no more than four of said shut-off devices.

3. The hemodialysis apparatus of claim 1, wherein said controlled circulation volume is at most 50% of the dialysis chamber volume.

4. The hemodialysis apparatus of claim 3, wherein said controlled circulation volume is at most 30% of the dialysis chamber volume.

5. The hemodialysis apparatus of claim 4, wherein said controlled circulation volume is about 20% of the dialysis chamber volume.

6. The hemodialysis apparatus of claim 1, wherein said balance chamber has a balance chamber volume that is at most ⅔ of the dialysis chamber volume.

7. The hemodialysis apparatus of claim 6, wherein said balance chamber volume is at most 50% of the dialysis chamber volume.

8. The hemodialysis apparatus of claim 7, wherein said balance chamber volume is at most 30% of the dialysis chamber volume.

9. The hemodialysis apparatus of claim 1, wherein said filling operating cycle and said circulating cycle have about the same time duration.

10. The hemodialysis apparatus of claim 1, further comprising a first fluid sensor connected between said dialysis fluid source and said fresh fluid partial chamber and a second fluid sensor connected between said dialysis fluid chamber and said used fluid partial chamber, wherein each of said first and second fluid sensors measures a respective fluid flow condition at its location and provides a corresponding signal to said control unit.

11. The hemodialysis apparatus of claim 1, further comprising the dialyzer, wherein the dialyzer comprises a semipermeable membrane dividing the dialyzer into a blood chamber and the dialysis fluid chamber.

12. The hemodialysis apparatus of claim 1, wherein said balance chamber has a balance chamber volume of at most 100 ml.

13. The hemodialysis apparatus of claim 12, wherein said balance chamber volume is at most 75 ml.

14. The hemodialysis apparatus of claim 13, wherein said balance chamber volume is about 30 ml.

15. The hemodialysis apparatus of claim 1, wherein said control unit is further connected for control transmission to each of said pumps and activates said first pump and deactivates said second pump during said filling operating cycle, and deactivates said first pump and activates said second pump during said circulating operating cycle.

16. The hemodialysis apparatus of claim 1, wherein said second pump and said ultrafiltration unit are arranged downstream from the dialysis fluid chamber of the dialyzer when the dialyzer is connected between said second and third shut-off devices.

17. A method of hemodialysis using an apparatus including only a single balance chamber divided by a displaceable partition wall into a fresh fluid partial chamber and a used fluid partial chamber, and including a dialyzer having a dialysis fluid chamber with a dialysis chamber volume, said method comprising the following steps:

(a) filling fresh dialysis fluid into said fresh fluid partial chamber and simultaneously draining used fluid from said used fluid partial chamber;

(b) circulating a controlled volume amount of said fresh dialysis fluid from said fresh fluid partial chamber into said dialysis fluid chamber while circulating a corresponding amount of used dialysis fluid from said dialysis fluid chamber into said used fluid partial chamber;

wherein said controlled volume amount is at most ⅔ of said dialysis chamber volume.

18. The method of claim 17, wherein said controlled volume amount is at most 50% of said dialysis chamber volume.

19. The method of claim 18, wherein said controlled volume amount is at most 30% of said dialysis chamber volume.

20. The method of claim 19, wherein said controlled volume amount is about 20% of said dialysis chamber volume.

21. The method of claim 17, wherein said step (a) of filling and draining fluid is carried out during a first time duration that is about the same as a second time duration during which said step (b) of circulating fluid is carried out.

22. The method of claim 17, wherein said steps (a) and (b) are separate non-overlapping steps carried out in succession, and further comprising a step of extracting a controlled amount of used dialysis fluid through an ultra-filtration unit arranged upstream of said used fluid partial chamber during said step (b).

* * * * *